(12) United States Patent  (10) Patent No.: US 8,851,675 B2
Hogan  (45) Date of Patent: Oct. 7, 2014

(54) HYBRID OCT SCANNING DEVICE

(76) Inventor: Josh N. Hogan, Los Altos, CA (US)

( * ) Notice: Subject to any disclaimer, the term of this patent is extended or adjusted under 35 U.S.C. 154(b) by 219 days.

(21) Appl. No.: 13/356,388

(22) Filed: Jan. 23, 2012

(65) Prior Publication Data

US 2012/0188509 A1 Jul. 26, 2012

Related U.S. Application Data

(60) Provisional application No. 61/461,975, filed on Jan. 26, 2011, provisional application No. 61/572,433, filed on Jul. 14, 2011.

(51) Int. Cl.
*G01B 9/02* (2006.01)
*A61B 3/10* (2006.01)

(52) U.S. Cl.
CPC ............ *A61B 3/102* (2013.01); *G01B 9/02091* (2013.01); *G01B 9/02069* (2013.01); *G01B 2290/65* (2013.01); *G01B 9/02058* (2013.01)
USPC ........................................... 351/217; 351/220

(58) Field of Classification Search
CPC ............................ A61B 3/102; G01B 9/02091
USPC .......................................... 351/216–217, 220
See application file for complete search history.

(56) References Cited

U.S. PATENT DOCUMENTS

| 5,321,501 | A * | 6/1994 | Swanson et al. | 356/479 |
| 6,267,477 | B1 * | 7/2001 | Karpol et al. | 351/221 |
| 7,872,759 | B2 * | 1/2011 | Tearney et al. | 356/479 |
| 2010/0284021 | A1 * | 11/2010 | Hacker | 356/497 |

* cited by examiner

*Primary Examiner* — Zachary Wilkes (57) ABSTRACT

The invention provides a hybrid OCT scanning device which improves OCT scanning of targets, including adaption for a ophthalmic targets (i.e. cornea, retina and fovea areas). The invention provides a movable beam modifying element which is adapted to be interposed in the probe radiation directed to the target, and the interposition of the movable element is synchronous with the periodicity of the OCT scan beam. The beam modifying element may include any of angular deflection regions, optical delay regions, or combinations of deflection and delay regions. Such regions of deflection and/or delay translate into a governable scan range, both lateral and depth, of a target region.

7 Claims, 6 Drawing Sheets

HYBRID OCT SCANNING DEVICE

CROSS REFERENCES TO RELATED PATENTS OR APPLICATIONS

This patent application claims priority from U.S. provisional patent application No. 61/461,975 titled "Hybrid Scanning System" filed on 26 Jan. 2011 and also claims priority from US provisional patent application No. 61,572,433 titled "Hybrid Angular Scanning System" filed on 14 Jul. 2011 and is related to U.S. Pat. No. 7,526,329 titled Multiple reference non-invasive analysis system and U.S. Pat. No. 7,751,862 titled Frequency resolved imaging system, the contents of both of which are incorporated herein as if fully set forth herein.

FIELD OF THE INVENTION

The invention described and illustrated in this application relates to non-invasive imaging and analysis techniques such as Optical Coherence Tomography (OCT). In particular it relates scanning mechanisms suitable for both time domain and Fourier domain OCT systems.

This invention also relates to the use of such OCT systems for non-invasive imaging and analysis of targets including, but not limited to: components of an eye; tissue; seeds; other biological or non-biological entities; concentrations of specific components or analytes in a target, such as the concentration of glucose in blood or tissue fluids. This invention also relates to analysis or monitoring for manufacturing defects in components for improved quality control.

BACKGROUND OF THE INVENTION

Non-invasive imaging and analysis of targets is a valuable technique for acquiring information about systems or targets without undesirable side effects, such as damaging the target or system being analyzed. In the case of analyzing living entities, such as human tissue, undesirable side effects of invasive analysis include the risk of infection along with pain and discomfort associated with the invasive process. In the case of quality control, it enables non-destructive imaging and analysis on a routine basis.

Optical coherence tomography (OCT) is a technology for non-invasive imaging and analysis. OCT typically uses a broadband optical source, such as a super-luminescent diode (SLD), to probe and analyze or image a target. It does so by applying probe radiation from the optical source to the target and interferometrically combining back-scattered probe radiation from the target with reference radiation also derived from the optical source.

The typical OCT optical output beam has a broad bandwidth and short coherence length. The OCT technique involves splitting the output beam into probe and reference beams, typically by means of a beam-splitter, such as a pellicle, a beam-splitter cube or a fiber coupler. The probe beam is applied to the system to be analyzed (the target). Light or radiation is scattered by the target, some of which is back scattered to form a back-scattered probe beam, herein referred to as signal radiation.

The reference beam is typically reflected back to the beam-splitter by a mirror. Light scattered back from the target is combined with the reference beam, also referred to as reference radiation, by the beam-splitter to form co-propagating reference radiation and signal radiation. Because of the short coherence length only light that is scattered from a depth within the target whose optical path length is substantially equal to the path length to the reference mirror can generate a meaningful interferometric signal.

Thus the interferometric signal provides a measurement of scattering properties at a particular depth within the target. In a conventional time domain OCT system, a measurement of the scattering values at various depths can be determined by varying the magnitude of the reference path length, typically by moving the reference mirror. In this manner the scattering value as a function of depth can be determined, i.e. the target can be scanned.

There are various techniques for varying the magnitude of the reference path length. Electro-mechanical voice coil actuators can have considerable scanning range, however, there are problems with maintaining the stability or pointing accuracy of the mirror. Fiber based systems use fiber stretchers, however, they have speed limitations and have size and polarization issues. Rotating diffraction gratings can run at higher speeds, however, are alignment sensitive and have size issues.

Piezo devices can achieve high speed scanning and can have high pointing accuracy, however to achieve a large scanning range requires expensive controls systems and have limited speed. A scanning method that effectively amplifies the scan range of a piezo device is described in U.S. Pat. Nos. 7,526,329 and 7,751,862 incorporated herein.

The technique described in these incorporated references uses multiple reference signals with increasing scan range and correspondingly increasing frequency interference signals. This scanning method can achieve large scan range at high speed with good pointing stability.

In swept source Fourier domain OCT systems depth scanning is accomplished by repeatedly sweeping the wavelength of the optical source. The wavelength range over which the optical source is swept determines the depth resolution. The period of the sweep repetition rate determines the period of the depth scans.

In addition to depth scanning, lateral scanning is required for many imaging and analysis applications. There are many conventional techniques for lateral scanning, such as the use of stepper or linear motors. Some applications require angular scanning, which is typically accomplished by electro-mechanical oscillating mirrors, typically referred to as salvo-scanners.

An example of an imaging application that requires angular scanning is the ophthalmic application of imaging the retina of the eye. The lens of the eye focuses collimated light on the retina. As a consequence lateral scanning by stepper or linear motors is not and effective retinal scanning technique. An angular scanning technique is required.

Conventional salvo-scanners are physically bulky and are inefficient because of their oscillating nature. They are therefore not suitable for compact or portable devices. There is therefore an unmet need for a method, apparatus and system for angular scanning over an extended depth range in a compact and power efficient manner.

SUMMARY OF THE INVENTION

The invention taught herein meets at least all of the aforementioned unmet needs. The invention provides a hybrid OCT scanning device which improves OCT scanning of targets, including adaption for a ophthalmic targets (i.e. cornea, retina and fovea areas). The invention provides a movable beam modifying element which is adapted to be interposed in the probe radiation directed to the target, and the interposition of the movable element is synchronous with the periodicity of the OCT scan beam. The beam modifying element may include any of angular deflection regions, optical delay regions, or combinations of deflection and delay regions. Such regions of deflection and/or delay translate into a governable scan range, both lateral and depth, of a target region. One embodiment of the invention provides hybrid scanning method and device which provides a means to insert angular deflection and optical delays into an OCT scanning system. The invention provides a hybrid OCT scanning device which improves OCT scanning of targets, including adaption for a ophthalmic targets (i.e. cornea, retina and fovea areas). The invention provides a movable beam modifying element which is adapted to be interposed in the probe radiation directed to the target, and the interposition of the movable element is synchronous with the periodicity of the OCT scan beam. The beam modifying element may include any of angular deflection regions, optical delay regions, or combinations of deflection and delay regions. Such regions of deflection and/or delay translate into a governable scan range, both lateral and depth, of a target region.

Such angular deflections translate into a governable scan range of some target region. Such optical delays extend the depth range scanned. In a preferred embodiment, the means of introducing angular displacement and optical delay is a rotating disc in the optical path of an OCT beam, where the disc contains multiple displacement elements effecting predetermined degrees of angular displacement and multiple optical delays effecting predetermined degrees of extended depth scan range or combinations of angular displacement elements and optical delays.

The movement of the disc is synchronized so that the set of scans obtained provide information that permits measurement or imaging of a predetermined scan area. In another embodiment of the invention, an axial displacement of the disc is included, which results in further governable aspects of the target site to be scanned. Examples of the inventive application include application in ophthalmology generally, and more specifically as a means of obtaining scan of cornea, retina and fovea areas.

DETAILED DESCRIPTION OF THE INVENTION

Figure 1:
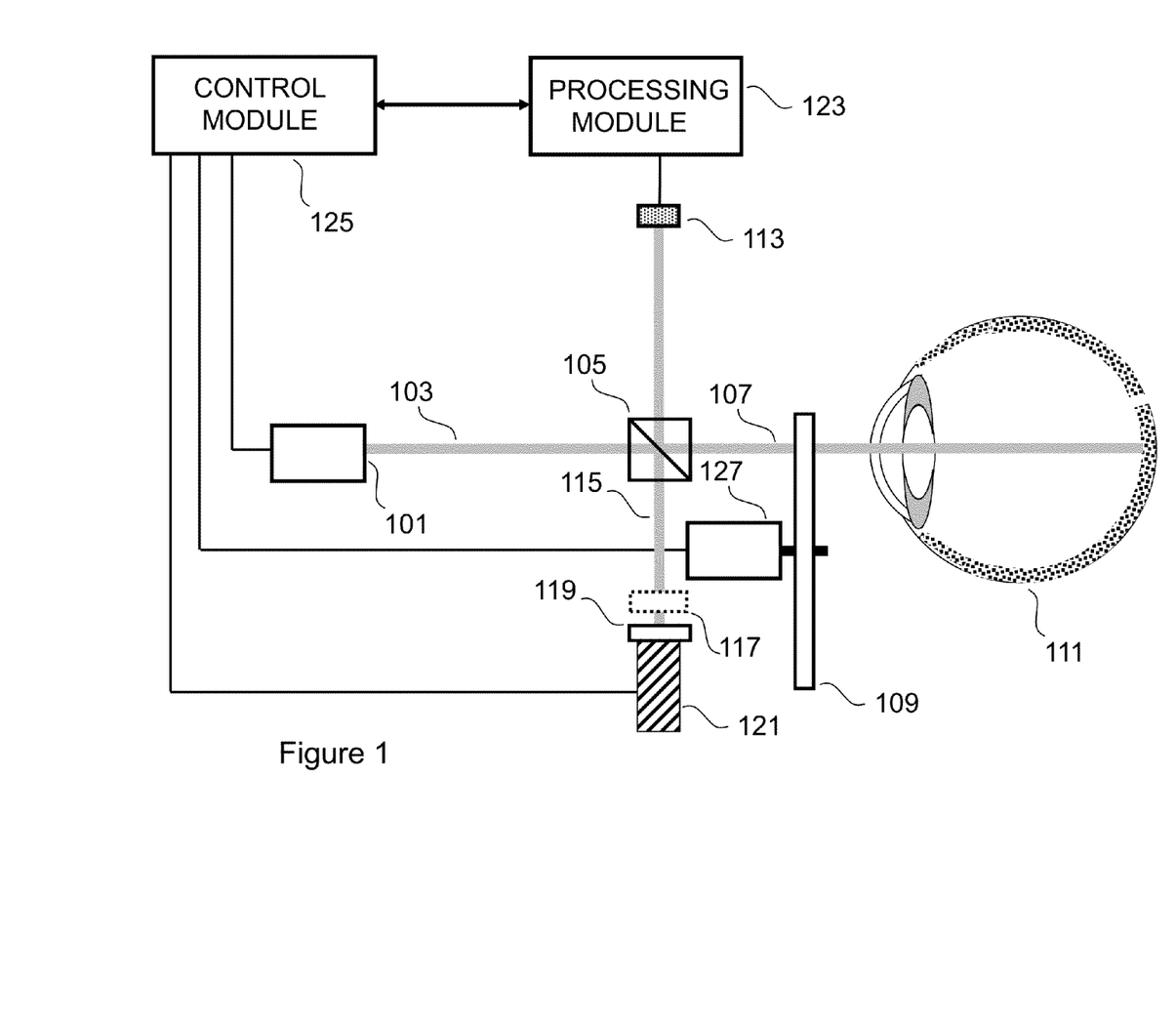
FIG. 1 is a schematic type illustration of a preferred embodiment of an OCT system that includes an angular scanning device according to the invention.

The preferred embodiment includes a time domain OCT system, an example of which is included in the FIG. 1 illustration where a broadband optical source 101 generates broadband output radiation 103, referred to as source radiation, that is directed at a beam-splitter 105. The beam-splitter 105 transmits a component of the source radiation as initial probe radiation 107 through a rotating disc 109 towards a target 111.

The rotating disc 109 can allow the initial probe radiation 107 to go directly to the target 111 or can introduce one or more beam modifying optical elements that can modify the optical radiation and allow at least a portion of the modified optical radiation to go to the target 111. While the preferred embodiment the beam modifying elements are housed in a rotating disc, in other embodiments the beam modifying elements could be housed in holders with many different configurations. For example, beam modifying elements could be housed in linear holder that moves laterally. Importantly the beam modifying elements are movable in a synchronous manner with respect to the repetitive scans of the OCT system.

Figure 2:
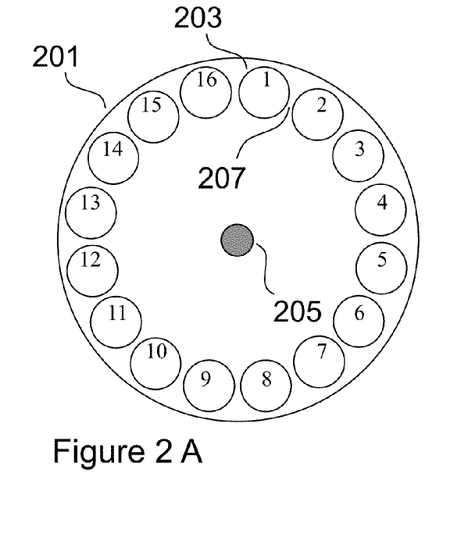
FIG. 2 is a more detailed illustration of a configuration of the angular scanning device.

The rotating disc, the beam modifying optical elements and their effect on the radiation directed at the target are all further described with respect to FIG. 2. Returning to FIG. 1, a portion of the initial probe radiation that is back-scattered from the target is directed by the beam-splitter towards a detector 113 and is referred to as back-scattered probe radiation.

The beam-splitter 105 also directs a component of the source radiation referred to as reference radiation 115 through an optical element 117 to a reference mirror 119 mounted on a translational device 121, such as a piezo device or an electro-mechanical translational device.

In the case of a conventional OCT configuration the optical element 117 is typically an attenuator used to optimize signal to noise (SNR) aspects. In the case of a multiple reference OCT configuration, further described in U.S. Pat. No. 7,526,329 titled Multiple reference non-invasive analysis system and U.S. Pat. No. 7,751,862 titled Frequency resolved imaging system (incorporated herein by reference), the optical element 117 is a partial reflective mirror which may also include an attenuator and in the case of a polarization OCT configuration may include a polarization rotating characteristic.

In the preferred embodiment the translational device 121 is a piezo device whose length is modulated by a periodic electronic drive signal (which determines the OCT scan periodicity).

A portion of the reference radiation 115, modulated by the translational device 121, propagates back through the beam-splitter 105 to the detector 113 where, in combination with the as back-scattered probe radiation it can generate one or more interference signals.

The interference signals are detected by at least one opto-electronic detector 113 whose electronic output is processed by a processing module 123 in conjunction with a control module 125 that provides electronic timing signals and drive signals to the piezo device 121, to a motor 127 rotating the disc 109 and optionally to the optical source 101.

The rotation of the disc 109 is synchronized with the repetitive length modulation of the piezo device. The disc is further illustrated in FIG. 2 where a disc 201 has 16 holes (of which 203, numbered 1, is an example) in which beam modifying optical elements can be located. The rotation of the disc 201 may be achieved by means of a shaft 205 at the center of the disc.

In the preferred embodiment the synchronization of the rotation of the disc with the repetitive length modulation of the piezo device causes the time the optical probe radiation encounters the solid regions between the holes in the disc (of which 207 is an example between holes number 1 and 2) to coincide with the turn around regions of the piezo device.

Rotation of the disc may be accomplished by either a linear or a stepper motor. In the case of a linear motor the beam modifying optical elements would typically be symmetric about the path that the optical beam traversed through the optical elements as the disc continuously rotated.

In the case of a stepper motor, the motor would move the beam modifying optical elements such that the optical beam is substantially centered on one of the beam modifying optical elements and then holds the disc stationary for a substantial percentage of the period of the repetitive length modulation of the piezo device.

Such synchronization ensures that the back-scattered optical signal is available for generating one or more interference signals during the most useful regions of the piezo scan (i.e. the regions between the turn around points).

In one preferred embodiment a movable beam modifying optical element would consist of an optical angular deflection element such as a holographic optical element whose design would pre-determine the magnitude of the optical angular deflection. Optical elements that do not cause angular deflection could be located in some holes (or they could be left empty or blank) and multiple different optical angular deflection elements could be located in the other holes.

FIG. 2B illustrates the case of the optical beam 215 propagating through a blank hole or an optical element that does not cause angular deflection in hole location numbered 1 of the disc 201 (of FIG. 2 A). (note using a non-deflecting optical element, rather than an empty hole, enables selecting or compensating for optical path length delays in order to depth align scans). The optical beam 215 propagates un-deflected to the target 209, which in this example is an eye. In this example the beam 215 is laterally aligned with the center of the cornea 211 and propagates in a straight line to be focused on the center of the foveal pit region 217 of the eye. (This lateral alignment can be accomplished with conventional positioning techniques.)

The disc 213 and shaft 205 (of FIGS. 2B and 2C) rotate to position an optical angular deflection element located in hole numbered 2 of the disc 201 (of FIG. 2 A) in the beam path. In this case the optical beam 221 is deflected by the optical element in the disc 213 resulting in an angularly deflected beam 223. Further rotation of the disc 213 causes multiple different optical angular deflection elements to be sequentially inserted into the path of the beam 221 resulting in the angularly deflected beam 223 to be deflected by multiple different angles.

In the target 209 example illustrated in FIG. 2C the angularly deflected beam 223 is further deflected by the lens of the eye (the target). This further deflected beam 225 is focused on the retina at a location 219 that is laterally displaced from the center of the fovea region 217. Similarly multiple different optical angular deflection elements cause the optical beam to be focused on different laterally displaced locations on the retina.

The figures Sheet 3 are in many respects similar to those of Sheet 2. In particular FIG. 3A illustrates the same rotation device 301 as 201 of FIG. 2A and FIG. 3B illustrates the same configuration as FIG. 2C. FIG. 3C illustrates an axial displacement of the rotating disc 313 of FIGS. 3B and 3C and thereby axial displacement of the pre-selected holographic optical element located in the rotating disc in the path of the optical beam.

While the magnitude of angular deflection achieved by introducing the pre-selected holographic optical element in the rotating disc 313 remains the same as that of FIG. 3B, the deflected beam 327 intersects a more outer region of the lens of the eye than does the deflected beam 323. The resulting further deflected beam 329 has an angular deflection of greater magnitude than does the further deflected beam 325.

The resulting lateral displacement along the retina to location 331 has a greater magnitude of displacement from the center location 217 of FIG. 2B than the displacement of location 333 from the center location 217.

The magnitude of the axial displacement 319 of the rotating disc 313 of both FIGS. 3B and 3C (and hence the magnitude of the axial displacement of the holographic optical element) can be systematically varied at a rate that is slow with respect to the period of the piezo modulation, while maintaining the same pre-selected angular deflecting holographic optical element, to generate a set of depth scans.

Figure 3:
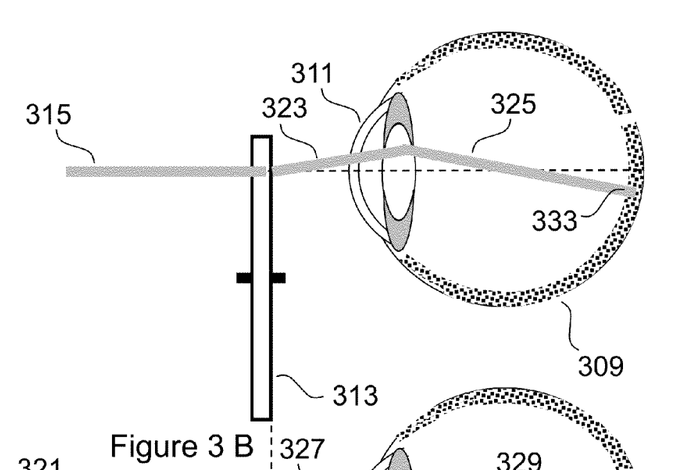
FIG. 3 is a more detailed illustration of an additional scanning aspect of the angular scanning device.
Figure 4:
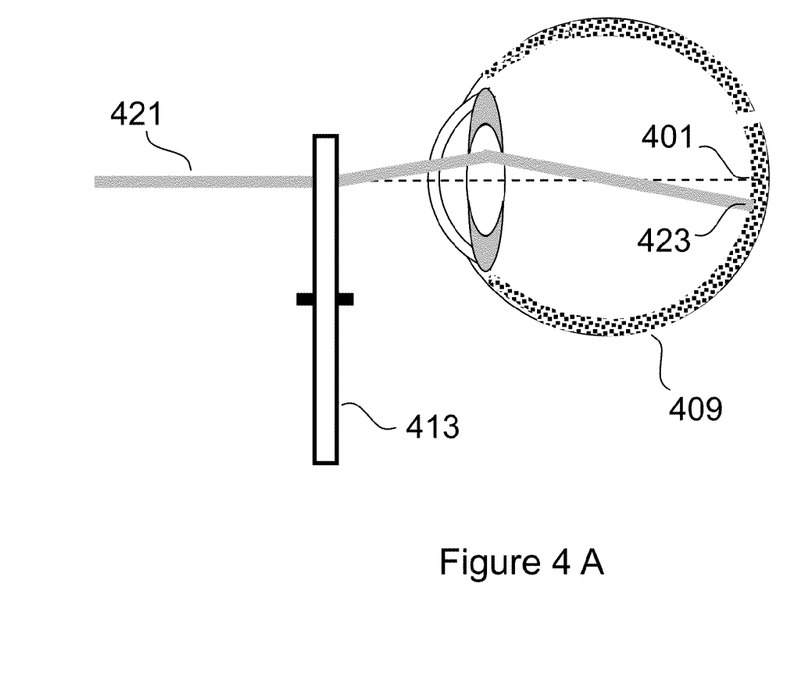
FIG. 4 is an illustration of aspects of an ophthalmic application.

Sheet 4 illustrates scan location patterns suitable for ophthalmic applications. FIG. 4A is similar to FIGS. 2C and 3B. A cross-section 403 of the retina centered on the foveal pit is depicted in FIG. 4B. The center of the foveal pit is shown as 401 in both FIGS. 4A and 4B.

FIG. 4C depicts a suitable pattern for mapping a region of the retina of the eye and locating the center of the foveal pit by repeated sets of scans accompanied by iterative lateral alignment of the OCT system with respect to the target (the eye). It shows six locations substantially symmetrically positioned on a circle indicated by the dashed circle 411 and a seventh location ideally in the center of the foveal pit.

The seventh and centered location would correspond to location 401 of FIGS. 4A and 4B. The laterally displaced location 423 of FIG. 4A would correspond to 413 of FIG. 4C (note drawings are not to scale for clarity).

A second scan pattern is depicted in FIG. 4D that includes the same depth scan locations as FIG. 4C with an additional six depth scan locations symmetrically positioned on the dashed circle 405. The pattern depicted in FIG. 4D could be achieved by loading the rotating disc 201 of FIG. 2 with non or zero deflecting optical elements in disc holes 1, 5, 9, 13 and twelve different angular deflecting optical elements in disc holes 2, 3, 4, 6, 7, 8, 10, 11, 12, 14, 15, 16.

In an alternative embodiment a disc with eight holes could be used with non or zero deflecting optical elements in disc holes 1 and 5 and six different angular deflecting optical elements in disc holes 2, 3, 4, 6, 7, 8. An axial displacement of the rotating disc 413 to scan at the additional outer six locations depicted on the dashed circle 405.

There are many variations of the described embodiments possible. For example, the number of optical elements in the disc could be other than sixteen or eight and their geometry could be other than circular. Other arrangements are possible such as two counter rotating discs. Instead of a rotating disc other geometries are possible, such as a rectangular synchronously sliding device more generally referred to as a carrier. Such a configuration is depicted in FIG. 6B where 605 is the first of a set of 16 beam modifying elements. One or more discs with more than one sets of beam modifying optical elements centered on circles of different radii could be used, as is depicted in FIG. 6A where a disc 601 ha a second set of beam modifying optical elements, one of which is 603, centered on a second smaller radius.

Holographic diffractive elements or other optical elements loaded in the rotating disc could also address focusing, wave front distortion, attenuation aspects. The beam modifying optical elements can be comprised of individual elements or various combinations of different types of elements that include, but are not limited to: an angular deflection element; an optical delay element; an attenuation element; a focusing element; a wave front distortion element.

While the preferred embodiment describes a time domain OCT system, other OCT configurations are included. Fourier domain swept source or spectral domain OCT systems could also avail of the invention. In these configurations rotation of the disc or carrier would be substantially synchronized with at least one of: periodicity of a piezo motion of an OCT reference mirror; periodicity of path length change of an OCT reference arm; periodicity of a Fourier domain OCT swept source.

Some applications, including some ophthalmic applications, require illumination of the target by light which may be of a similar wavelength to that used by the OCT system (typically to assist in lateral alignment of the OCT system with respect to the center of the cornea of the eye). Embodiments with such requirements, with or without a rotating disc, could eliminate undesirable optical cross-talk or interference between the OCT light and the target illuminating light by pulsing the illuminating light synchronously with the periodicity of the piezo motion (or other length modifying device) of an OCT reference mirror and phase aligned with un-useful turn around time of the piezo device.

Alternatively the pulsed illuminating light could be pulsed synchronously with a multiple of the period of the piezo motion or in the case of a Fourier domain OCT system, the period of the swept source. In such an approach, OCT information acquired during periods when the illuminating light is pulsed on would be discarded or at least processed differently.

In alternative embodiments the patterns depicted in FIGS. 4C and 4D could be depth aligned with a surface other than the retina, such as a surface of the cornea or a surface of the intra-ocular lens. They could also be aligned to locate the center region of the optic nerve.

The axial displacement approach could be used to repeatedly scan radially across the retina to generate a set of scans to image one or more (radially rotated) cross-sections of the retina, typically centered on the foveal pit.

The axial displacement approach could be used to scan from the center of the foveal pit to the optic nerve to determine the distance between the foveal pit and the optic nerve.

Multiple locations, either randomly distributed or according to a pre-determined pattern, on the retina could be depth scanned to monitor for malignant characteristics of the retina. Pre-determined pattern could be used to generate one or more images of retina regions.

Figure 5:
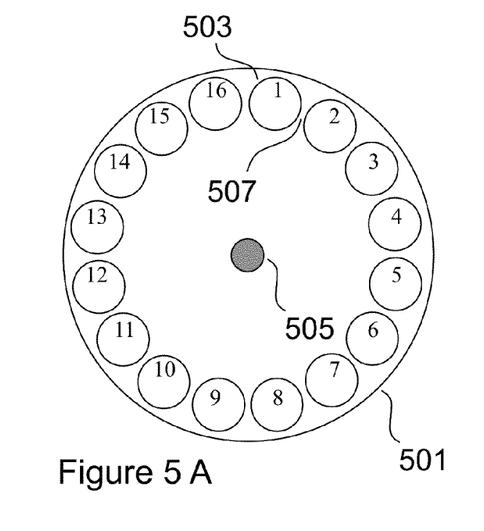
FIG. 5 is an illustration of aspects of a configuration of the stepped optical delay elements and their relationship with scan segments.

In another preferred embodiment a beam modifying optical element would consists of an optical delay element such as a glass element whose thickness and refractive index would pre-determine the magnitude of the optical delay. This embodiment is illustrated in FIG. 5. Locating a similar optical delay element in all of the odd numbered holes (1, 3, 5, 7, 9, 11, 13, 15 in the example of disc 501) and leaving the even numbered holes empty would enable the scan depicted in FIG. 5B.

In this embodiment the system would perform a scan at a deeper region 511 of the target 509 during the time that the (empty) even numbered holes of the rotating disc 513 are aligned with the probe radiation. Rotation of the disc to align the odd numbered holes containing similar optical delay elements with the probe radiation introduces the pre-determined delay in the optical path and as a consequence as second region 515 of the target 509 to be scanned where the second region 515 is offset in depth from the first region 511 by an amount determined by the optical delay.

As depicted in FIG. 5B the system could be aligned to have first region 511 be the main region of interest within the target and the optical delay chosen to locate the second region 515 to scan the front surface of the target, thus providing a method of registering the location of the first scan with respect to the front surface.

In this embodiment one of the two scans is used to register the location of the other scan by having one scan scanning a region of the front surface, and the other scan at a predetermined (by virtue of the predetermined delay introduced into the optical path), known depth.

Another embodiment is illustrated in FIG. 5C which again has a target 517 and the rotating disc 519 and where a set of nine overlapping scan segments are depicted in the oval 521. Every second of the scan segments within the oval 521 is offset for illustration clarity only.

In a preferred embodiment the nine scan segments would be accomplished by having pre-determined optical delays have more than one value. In this embodiment again the odd numbered holes of the rotating disc 513 contain similar optical delay elements (to provide the same optical delay) and are depth aligned to scan the front surface of the target 517.

The eight odd numbered holes contain different optical delay elements with eight different values that are systematically smaller in magnitude (with the smallest optionally being empty). As the disc 519 rotates delays are introduced that have eight different values with a ninth value introduced between each of the eight other values. The resulting scan consists of nine scan segments at different, known depths, as depicted in the oval 521.

In this manner the rotating disc 519 containing the optical delay elements is a device that is synchronously interposed in the optical path, which effectively permits controlled and selectable delay magnitudes.

The different optical delay elements may also include attenuation (such as ND filters) with different magnitudes that are associated with different magnitudes of delay. A preferred embodiment would include attenuation that increases in magnitude with increasing optical delay magnitude to allow reducing of the magnitude of the less deep signals (whose magnitude are typically larger) in order to optimize dynamic range.

In the preferred embodiments described above, in addition to (or in place of) different attenuation being associated with different optical delays different focusing properties could be associated with different optical delays to compensate for different target associated focusing properties.

In the preferred embodiments described above, the odd numbered optical delay elements would correspond to forward motion of the piezo device while the even numbered optical delay elements would correspond to reverse motion of the piezo device (or visa versa). Other arrangements are possible, for example the rotating disc could be synchronized such that the opaque disc regions (one of which is 507) coincides with the same turn around region of the piezo scan (at one extreme rather than alternating between the two extremes).

Figure 6:
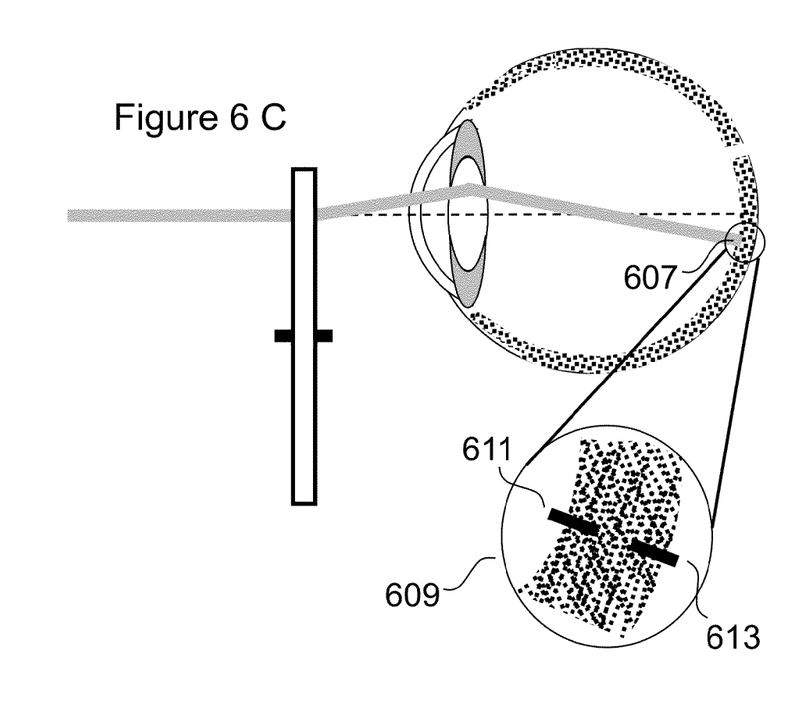
FIG. 6 is a an alternate example of movable beam modifying element (disc and linear) and an example of the effect of two beam modifying elements with the same angular deflection but different optical delays.

Many other embodiments of the invention are possible. For example, angular deflection elements could be combined with optical delay elements as a single beam modifying optical element. An example is depicted in FIG. 6 C which in many respects is similar to FIG. 3 C however the portion of the retina 607 which is shown in greater detail in the circle 609 shows a scan 611 of the surface region of the retina and a scan 613 of a deeper region of the retina. In this example one beam-modifying element would accomplish an angular displacement and an optical delay, while a second beam modifying element would accomplish the same angular displacement but a larger optical delay.

Other examples will be apparent to persons skilled in the art. The scope of this invention should be determined with reference to the specification, the drawings and the appended claims, along with the full scope of equivalents as applied thereto.

The invention claimed is:

1. A device for performing a repetitive OCT scan of a target wherein said device comprises:
    an OCT system adapted to perform one or more depth scans of a target, including a probe beam; and
    a movable beam modifying element selectably interposable in the optical path of said probe beam, said movable element adapted to introduce modification of said optical path synchronous with respect to periodicity of the OCT scan,
    wherein said movable beam modifying element is adapted to introduce depth variations, and said movable element comprised of pre-selected delay elements, so that the interposition of the movable beam modifying element in the optical path of said probe beam is synchronous with the periodicity of the scan beam, so the scan beam periodically passes through regions of predetermined delay, resulting in a scan that includes at least two scan portions offset depthwise from each other,
    where said device is adapted to perform a continuous scan and, synchronous with said continuous scan, said moveable beam modifying element is adapted to introduce delay into the optical path of the beam which effectively moves the scan position in depth (with respect to the surface of the target), such that the output of said performed scan includes at least two continuous scan portions offset in depth from each other;
    wherein said moveable beam modifying element is comprised of pre-selected regions of predetermined delay, so that interposition of said movable beam modifying element in said optical path is synchronous with the periodicity of the scan beam, so said scan beam periodically passes through regions of predetermined delay, resulting in a scan that includes at least two continuous scan portions offset in depth from each other;
    where said movable beam modifying element contains predetermined regions, and each said region characterized by some value of delay with respect to the optical path, where said regions may be controllable introduced into said optical path so as to produce correspondingly controllable delays;
    wherein said predetermined regions of said movable beam modifying element are further characterized by some optical property including:
    regions of predetermined differing, magnitudes of attenuation, such that different delays provide different attenuation, increasing as delay magnitude is increased, allowing reducing of the magnitude of the less deep signals; and
    regions of predetermined differing magnitudes of compensation for differing, associated focusing properties.

2. The device of claim 1 wherein said movable beam modifying element is adapted to introduce angular deflection, and said movable element is comprised of pre-selected deflection elements, so that the interposition of the movable beam modifying element in the optical path of said probe beam is synchronous with the periodicity of the scan beam, so the scan beam periodically passes through regions of predetermined angular deflection, resulting in a scan that includes at least two scan portions offset laterally from each other.

3. The device of claim 2, wherein said wherein said movable beam modifying element is axially displaced resulting in at least one scan whose lateral offset is also determined by the magnitude of the axial displacement.

4. The device of claim 3, wherein said magnitude of said axial displacement is systematically varied to achieve a set of depth scans spanning a region of the target.

5. The device of claim 4, wherein said device is adapted for the target where the target is an eye and the region of the target spanned is a substantially linear region which includes the foveal pit, enabling an image of the foveal pit.

6. The device of claim 5, wherein said device is adapted for the target where the target is an eye and the region of the target spanned includes the foveal pit and the optic nerve.

7. The device of claim 6, wherein said movable beam modifying element undergoes continuous axial displacement resulting in at least one scan set suitable for measuring a distance or generating an image.

* * * * *